US 6,709,871 B2

(12) United States Patent
Anderson

(10) Patent No.: US 6,709,871 B2
(45) Date of Patent: Mar. 23, 2004

(54) PRECISION FLUID GRADIENT FORMATION

(75) Inventor: Norman G. Anderson, Rockville, MD (US)

(73) Assignee: Large Scale Proteomics Corporation, Vacaville, CA (US)

(*) Notice: Subject to any disclaimer, the term of this patent is extended or adjusted under 35 U.S.C. 154(b) by 222 days.

(21) Appl. No.: 09/859,504

(22) Filed: May 18, 2001

(65) Prior Publication Data

US 2002/0131894 A1 Sep. 19, 2002

Related U.S. Application Data

(63) Continuation-in-part of application No. 09/573,539, filed on May 19, 2000, now abandoned.

(51) Int. Cl.[7] .................................................. G01N 1/00
(52) U.S. Cl. ...................... 436/174; 436/183; 436/177; 435/325
(58) Field of Search .............................. 436/177, 183, 436/174; 435/325, 239; 424/88; 210/361, 789; 422/70, 72, 77

(56) References Cited

U.S. PATENT DOCUMENTS

| | | | |
|---|---|---|---|
| 3,519,400 A | | 7/1970 | Anderson |
| 3,863,901 A | | 2/1975 | Janda et al. |
| 4,096,035 A | * | 6/1978 | Machlowitz et al. ...... 435/252.1 |
| 4,290,300 A | | 9/1981 | Carver |
| 5,496,517 A | | 3/1996 | Pfost et al. |
| 5,922,211 A | | 7/1999 | Nees |

OTHER PUBLICATIONS

Gen. Chem., Ebbing, "Diluting Solutions." Houghton Mifflin Com. Pp. 74–79, (1984).

J. Chem. Ed., Guenther, "Density Gradient Columns for Chemical Displays," Gilbert, ed. vol. 63, No. 2, pp. 148–150, (1986).

* cited by examiner

Primary Examiner—Jill Warden
Assistant Examiner—Yelena G. Gakh
(74) Attorney, Agent, or Firm—John E. Tarcza; John C. Robbins

(57) ABSTRACT

Ways for reproducibly making liquid gradients with a high degree of precision are provided. Different regions in the gradient are preformed by premixing liquids usable for other components of the gradient to form an intermediate gradient component that is then added to the vessel. The system is particularly adapted for making non-linear and multiple overlapping different gradients in the same liquid in the same vessel.

30 Claims, 10 Drawing Sheets

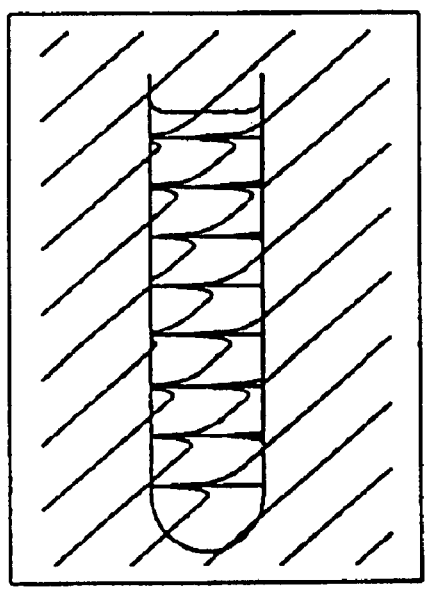
Fig. 6A
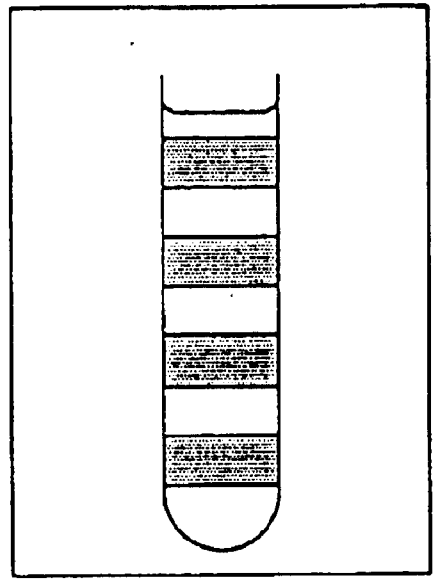
Fig. 6B
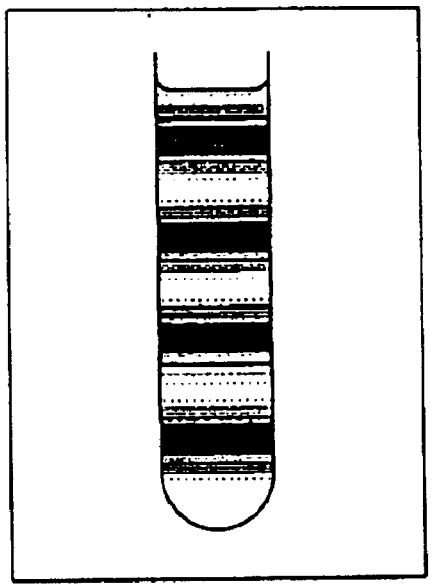
Fig. 6C
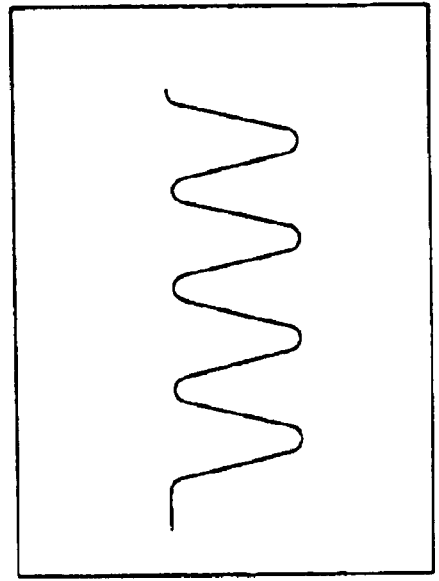
Absorbance
Fig. 6D
Figure 6

PRECISION FLUID GRADIENT FORMATION

This is a continuation-in-part of Ser. No. 09/573,539 filed May 19, 2000 now abandoned.

FIELD OF THE INVENTION

The present invention relates the formation of both linear and non-linear liquid gradients from liquids having very small density differences, and to the formation of gradients having different reagents in different levels of the gradient. The invention further relates to the formation of sets of gradients in parallel. These are particularly useful for fractionation of cellular or subcellular particles from biological samples.

BACKGROUND OF THE INVENTION

Liquids having gradients of temperature, concentration, density and color have been previously prepared. Liquid density gradients have been used for many years, for a variety of purposes, in a number of different industries. The inventor has numerous publications and patents regarding certain aspects of gradient formation and use including: Anderson, N. G. Mechanical device for producing density gradients in liquids. Rev. Sci. Instr. 26: 891–892, 1955; Anderson, N. G., Bond, H. E., and Canning, R. E. Analytical techniques for cell fractions. I. Simplified gradient elution programming. Analyt. Biochem. 3: 472–478, 1962; Anderson, N. G., and Rutenberg, E. Analytical techniques for cell fractions. A simple gradient-forming apparatus. Anal. Biochem. 21: 259–265, 1967; Candler, E. L., Nunley, C. E., and Anderson, N.G. Analytical techniques for cell fractions. VI. Multiple gradient-distributing rotor (B-XXI). Anal. Biochem. 21: 253–258, 1967.

A variety of other methods for making density gradients have been developed, and Bock, R. M. and Ling, N. S., Analyt. Chem 26, 1543 (1954), and Morris, C. J. O. R, and Morris, P., Separation Methods in Biochemistry, Pitman Publishing, $_2$nd ed., 1976, have reviewed many of these. Only one of these methods allows gradients to be made from multiple solutions, each having a different combination of reagents (Anderson, et al., "Analytical Techniques for Cell Fractions. I. Simplified Gradient Elution Programming", *Analytical Biochemistry* 3: 472–478 (1962).) Innovations that are more recent include the use of pumps and pistons, which are differentially controlled by microprocessors, e.g., the Angelique gradient maker (Large Scale Proteomics Corp. Rockville, Md.). Gradients may also be generated during centrifugation by sedimenting a gradient solute such as cesium chloride or an iodinated x-ray contrast medium such as Iodixanol®. Additional references discussing such methods are mentioned in the References section below. The large number indicates the importance of the problem of gradient making.

Density gradients are used to make two basic types of separations. The first separates particles based on sedimentation rate (rate-zonal centrifugation), in which particles are separated based on the size and density and to a lesser extent their shape. The particles will sediment farther if centrifuged for a longer period of time. The second method separates particles based on isopycnic banding density, in which particles reach their equilibrium density level, and do not sediment further with continued centrifugation.

SUMMARY OF THE INVENTION

One object of the present invention is to produce segments of a liquid density step gradient which differ predictably in their properties, and in the identity and concentration of reagents present in individual segments.

It is a further object to make all aspects of sample and gradient production and centrifugation identical so that the gradients are reproducible.

It is another object of the present invention to prepare a liquid having plural gradients of different types.

It is yet another object of the present invention to mix gradient components to prepare intermediate gradient components for accurately generating fine differences in the gradient.

It is yet a further object of the present invention to use liquids with small density differences to lessen the irregularities in forming a gradient.

Another object of the present invention is to make the sedimentation through a gradient an analytical process for analytical particle recovery from the liquid gradient and analytical measurement of particles in the gradient.

A further object of the present invention is a means for producing individual segments of the gradient.

It is still another object of the present invention to use a microprocessor to control and schedule an automatic pipetting system to produce multiple gradient segments in which the difference between each gradient segment is small and suitable for producing narrow zones which may be evened out by timed diffusion.

It is another object of the present invention to control the temperature of all steps in the gradient production and gradient recovery process and to avoid temperature induced mixing.

It is a further object of the present invention to provide means for making linear and complex non-linear gradients.

It is another object of the present invention to provide means for subfractionating biological particles by sedimenting them through zones of reagents with which the particles interact.

It is a further object of the present invention to construct complex gradients in which gradient stability is conferred by an inert component while superimposed gradient reagents extract or separate certain particles or constituents from the particles sedimenting through the gradient, leaving the extracted constituents at their extraction levels.

The present invention achieves these objectives by using a large number of gradient components where fine differences are achieved by mixing one gradient component with another to prepare an intermediate gradient component. Additional intermediate gradient components may also be similarly made. Even if the exact concentration is uncertain, the range must be correct. This technique assures that inversions and other irregularities do not occur. This technique is also readily automatable and can prepare multiple gradients in the same solution. Of particular benefit is the inclusion of a reagent with specialized properties within a particular region of the gradient to enhance separation and recovery of the sample particles.

Preferred uses are for separation and quantification of biological particles in a reproducible manner.

BRIEF DESCRIPTION OF THE DRAWINGS

FIG. 6A is a Schlieren pattern of a step gradient before diffusion.

FIG. 6B is a gradient with a colored compound being added to alternating layers of a step gradient.

FIG. 6C is the gradient of FIG. 4B after it has diffused to form a linear gradient.

FIG. 6D is an optical scan of the colored compound in the gradient of FIG. 6C.

DESCRIPTION OF THE PREFERRED EMBODIMENTS

Figure 1:
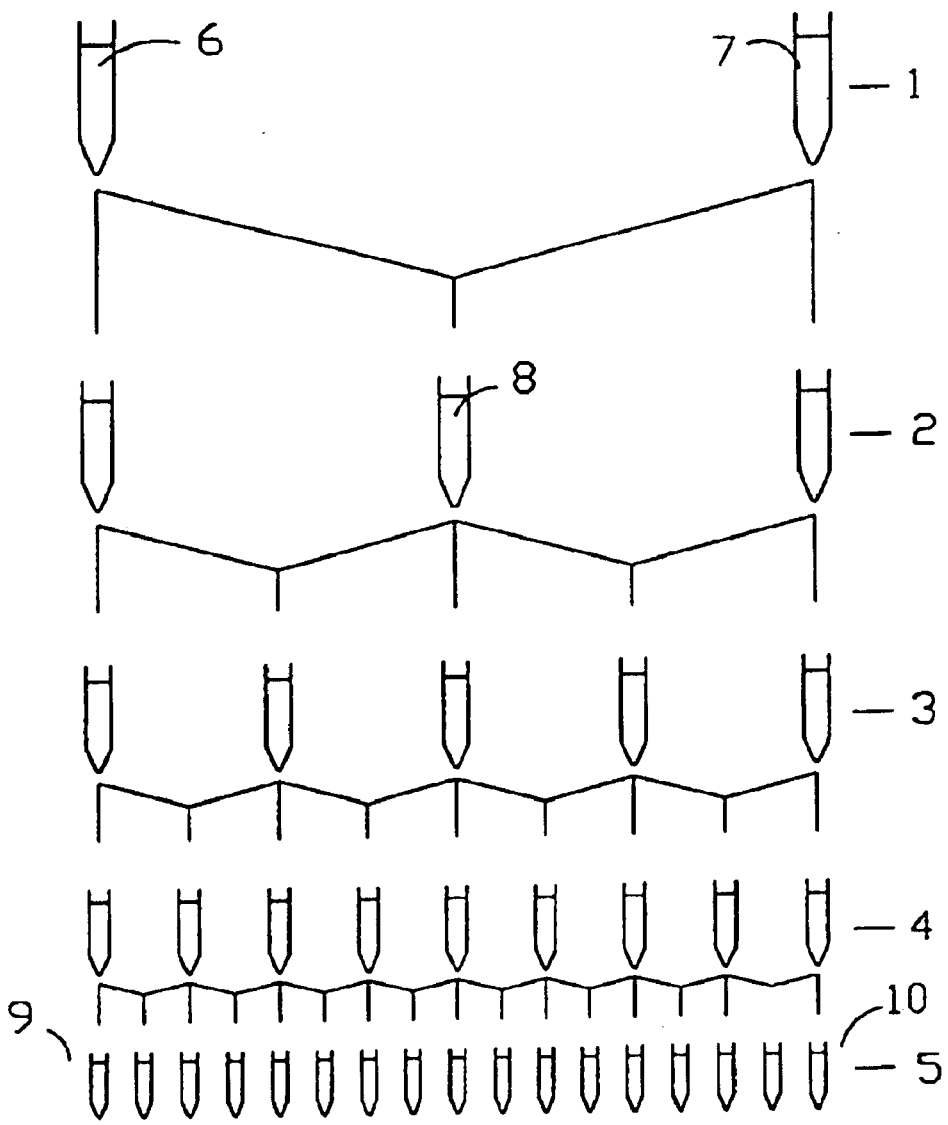
FIG. 1 shows a mixing pattern for linear gradient construction and how finely graded intermediate level gradient components are prepared.

The term "gradient" includes a non-homogenous fluid composition where one portion contains a quantitative difference in a particular property from another portion. The differences may be in concentration, density, color, temperature, osmotic pressure, absorbency, particle amount or size, electrical and magnetic properties such as resistance, etc. For the present invention, density and concentration gradients are generally of most interest. The gradient need not be completely stable if it is controllable for a period of time.

A "linear gradient" is a gradual, even and constant change in a gradient property from one end of the gradient to an opposite end.

A "step gradient" is an abrupt change in the gradient property between two fluid portions in the gradient. It is typically made by layering one liquid over a different liquid.

A "non-linear gradient" is a gradient with an uneven distribution of or non-constant change in the gradient over the length of the gradient. While step gradients are non-linear, others such as exponential or irregular are also considered non-linear gradients.

A "gradient component" is a homogenous fluid having a particular property that is desired to be located in a particular region of a gradient. For example, to create a gradient, one requires at least two gradient components or solutions unless the gradient is self-forming (e.g. cesium chloride gradients). The gradient components being used to create a gradient may contain different amounts of a compound, composition, particle etc, (same features), or may contain chemically or physically different features (compounds, compositions, particles etc.). A large number of different gradient components are known per se.

A "reagent capable of reacting" includes any composition that engages in an interaction such as binding, catalysis, chemical reaction, precipitation etc.

An "intermediate level" gradient component is one which is known to have a property intermediate between two other gradient component materials because the intermediate level gradient component is formed by mixing one gradient component material with another gradient component material. The term "intermediate level" is not meant to mean exactly intermediate. Instead the term is used to indicate a level more similar to one parent gradient component than another.

A "secondary intermediate level" gradient component results from mixing an intermediate level gradient component with another gradient component material which itself may be an intermediate level gradient component. "Tertiary", "quaternary" etc. intermediate level components are also so formed in a like manner. In each situation, the resulting gradient material will be intermediate between the two gradient component materials used to form it.

A "sedimentation container" is a vessel that a sample is allowed to or is forced to pass through. Centrifuge tubes are typical sedimentation containers for small particles. For larger particles, the force of gravity is sufficient to sediment such particles. Separation is enhanced by a density gradient in the sedimentation container.

The term "isolated", when referring to a particle or macromolecule, means that it is essentially free of other components originally found in the sample. The term "purified" refers to a state where the relative concentration of a particle or macromolecule is significantly higher than in the starting composition before it is purified. Purity and homogeneity are typically determined using standard analytical techniques.

Generally, a purified or isolated product will comprise more than 80% of all similar species present in the preparation. Preferably, the product is purified to greater than 90% of all species present. More preferably, the product is purified to greater than 95% and most preferably, the product is purified to essential homogeneity, or wherein other species are not significantly detected by conventional techniques.

The term "protein" is intended to also encompass derivatized molecules such as glycoproteins and glycolipids as well as lower molecular weight polypeptides.

The term "bind" includes any physical attachment or close association, which may be temporary or permanent as in a chemical bond. Generally, an interaction of hydrogen bonding, hydrophobic forces, van der Waals forces etc. facilitates physical attachment between the ligand molecule of interest and the receptor. The "binding" interaction may be brief as in the situation where binding causes a chemical reaction to occur. This is typical when the binding component is an enzyme and the analyte is a substrate for the enzyme. Reactions resulting from contact between the binding component and the analyte are within the definition of binding for the purposes of the present invention. Binding is preferably specific. The binding may be reversible, particularly under different conditions.

The term "bound to" or "associated with" refers to a tight coupling of the two components mentioned. The nature of the binding may be chemical coupling through a linker moiety, physical binding or packaging such as in a macromolecular complex. Likewise all of the components of a cell are "associated with" or "bound to" the cell.

Experimentally it is quite difficult to make a long series of solutions for use in making a complex non-linear gradient without considerable effort, especially when the density differences between some steps are very small.

The present invention achieves its objectives by using a large number of gradient components where fine differences are achieved by mixing one gradient component with another to prepare an intermediate gradient component. Additional intermediate gradient components may also be similarly made. This technique is also readily automatable and can prepare multiple gradients using the same set of basic solutions.

Precision gradients are difficult to make in practice, and it is further difficult to confirm that a set of gradient components is identical to previously made gradient components without destroying them for analysis.

Existing swinging bucket rotors generally allow six gradients to be centrifuged simultaneously, while larger numbers may be centrifuged if lower resolution of the vertical or near vertical tube rotors is accepted. Therefore, if existing density gradient formers were to be used, a set of six or more of them operating in parallel will be required.

The present invention involves a system for producing liquid density gradients by using a series of liquids of increasing density prepared by mixing a starting set of liquids of differing density. This is performed using an automatic microprocessor controlled system for pipetting and mixing the liquids according to a set or adjustable computer program, and a device for introducing aliquots of the series of liquids into centrifuge tubes to produce a gradient. It is particularly desirable that uniformly sharp interfaces can be made between the individual liquids in the gradients whether they are density gradients or a different type of gradient.

When preparing an exact intermediate gradient component liquid, it is preferred to use equal volumes or equal weights of each parent liquid. The choice of liquids to mix and formation of intermediate gradient liquids may be set according to a prescribed pattern, conveniently determined by a computer controlled by a set of instructions to use the prescribed pattern. One may omit forming some of the final set of liquids if not employed to make a gradient component or necessary to prepare an intermediate for a secondary intermediate as a gradient component. By carefully controlling the volume or weight of each parent liquid, one may directly prepare the final gradient component to be added to the sedimentation vessel. In such a situation, one need not make intermediate liquids which are used only to make other intermediate liquids.

One advantage of using multiple-step gradients is that they will reproducibly convert from step to continuous gradients by diffusion over time. This occurs more rapidly and reproducibly if the steps are small. Additionally, the smaller the steps, the tighter the control, a particular advantage with non-linear gradients. With non-linear gradients, one may have a first interface between steps, which is very small, and a second interface between steps, which is very large. One can optimize diffusion time for one interface but it will not be optimal for the other interface and may even result in destabilization of the density gradient. By using many steps, these problems are minimized. With non-linear gradients, it may be preferred to have uneven sized steps to compensate for uneven differences in the step gradient components and uneven amounts of liquid for various steps.

Many reasons exist for controlling gradient shape. Gradient capacity (i.e., the mass of particles which can exist in a zone without causing a density inversion) is a function of gradient slope, and a steep gradient can support a greater mass of particles per unit gradient length than can shallow gradients. The greatest particle mass concentration in a gradient separation usually occurs immediately beneath the sample zone shortly after centrifugation or other sedimentation has started. As different particles separate in the length of the gradient, the possibility of an overloaded zone diminishes. For this reason, it is desirable to have a short steep gradient section immediately under the sample zone, followed by a shallower gradient section.

It is particularly important to avoid inversions, as they may be unstable, trap particles at the wrong location and render the gradient needlessly overly complex. When preparing gradients, either linear or non-linear, it is desirable to have many short step gradient components to avoid formation of an inversion. Additionally, when adding a sample to the top of a gradient, occasionally one generates an inversion due to local interface conditions. Any inversion in the gradient further magnifies the irregularity. As sample components attempt to pass through the gradient too rapidly they may pull a mixture of components through the gradient which otherwise would not so pass. Such local inversions are reduced using the present invention that permits a smoother gradient to be formed.

When using an intermediate solution, even if a mistake is made in the preparation, an inversion cannot exist. When preparing multiple intermediate solutions, it is possible for a mistake to create an inversion but it is less likely than preparing each gradient component from raw materials.

While the emphasis is on density gradient formation, the same principles may be applied to other gradients, such as concentration and other gradients as well.

One of the reasons for having different compositions throughout a gradient is that different particles have different requirements for stable separation and/or isolation. For example, in subcellular particle purification, ionic and osmotic requirements for each particle's optimal isolation differ from each other. Likewise, different portions of the density gradient may have essential cofactors, aggregating components, e.g. antibodies, receptors, optionally with detectable labels, that bind to a desired component, solvents and other disaggregating components, e.g. hydrolases, etc. Minor additions may be made to a gradient zone, for example, an enzyme may be added dry to tube 23, without changing the gradient noticeably. Mixing of constituents may be done by rotational agitation of the plate, or by pipetting mixtures up and down using an automatic pipetter.

By using more gradient steps and different gradients superimposed on each other complex gradients may be produced, e.g. a density gradient and a salt gradient superimposed on or an osmotic band included in the density gradient. These complex gradients have several advantages depending on what one is separating.

Complex gradients may have a concentration of density material may be very different from concentration of non-density material (e.g. a solvent), which may be very different from a macromolecule material (e.g. an enzyme) as long as each material is not a sedimentable particle that would be moved substantially by the sedimentation process. Each gradient component may be in a linear or non-linear format independently.

As is shown in FIG. 6A, local step gradient interfaces can be observed using a simplified Schlieren system suitable for round tubes (Anderson, A Simple Method for Observing Refractive Index Gradients in Liquids. Biochim. Biophys. Acta 25: 418 (1957). Alternatively, a dye or suitable colored substances having a diffusion coefficient close to that of the major gradient solute may be used. It is desirable to use a readily detectable component with approximately the same molecular weight as the density gradient material so that both will codiffuse together. Cobalamine (Mw=1355) has a bright red color, and provides a suitable diffusion indicator for Iodixanol® {5, 5'-[(2-hydroxl-1-3 propanediyl)-bis (acetylamino)] bis [N,N'-bis (2,3dihydroxypropyl-2,4,6-tiriiodo-1,3-bezenecarboxamide,MW=1550}. A step gradient formed with cobalamine as an indicator is shown in FIG. 6B immediately after it has been formed. It is optional to use a readily detectable component with approximately the same molecular weight as the density gradient material so that both will codiffuse together. Other readily detectable components may also be used and detected by a variety of different techniques. When an optical scan (or other appropriate scan depending on the detection method) of the tube yields a continuous sine wave (FIG. 6D), the gradient is even enough to be used. Other readily detectable components may also be used and detected by a variety of different techniques.

Four types of gradients are in general use with either of these basic methods. The first includes step gradients, made by layering a series of solutions of decreasing density.

The second type comprises continuous linear gradients that may be made by a mechanical gradient maker. The gradient may be introduced slowly through small tubing to the bottom of the centrifuge tube. For ease of application, liquid gradient components may be pumped through the small tubing or the small tubing may have a funnel attached thereto for easy addition of liquids.

The third type of gradient is non-linear, and may be designed to separate particles having a very wide range of sizes or densities. Non-linear gradients may be designed to separate particles on the basis of either sedimentation rate or isopycnic banding density, or both types of separations may occur in the same gradient, in which case some particles reach their isopycnic level at some point in the gradient, while others are still sedimenting. Generally such combined separations involve larger and denser particles which band near the bottom of the gradient, while other smaller, and usually lighter particles are still sedimenting in the upper portion of the gradient.

The fourth type of gradient is one generated in a high centrifugal field by sedimentation of the major gradient solute. In such a situation, the gradient is formed by the action of the centrifugal field.

Particles, which differ little in sedimentation rate, are preferably separated by sedimenting them through a longer shallower section of the gradient, which may be located near the center of a gradient. By contrast, particles with widely differing sedimentation rates may be separated through a steeper section of the gradient.

To retain rapidly sedimenting particles, such as cell clumps or whole cells, a steep gradient section may be included near the bottom. Particles may be retained either because they sediment more slowly through this concentrated, and often viscous section, or because they band isopycnicly.

During sedimentation, once separation has occurred into relatively distinct bands, one may continue or increase the force of sedimentation to drive the bands to stack up at the bottom of the sedimentation vessel. Typically, one may simply change the centrifuge speed to enhance the rate of sedimentation. To do this, particles are separated based on sedimentation coefficients. Provided that the absolute density of the gradient components does not cause isopycnic banding, the particles will stack up at the bottom of the sedimentation vessel in layers. Individual layers may then be removed easier than attempting to remove fluid bands. To facilitate thicker layers for easier separation, the sedimentation vessel has a preferably smaller cross section toward the bottom section of the sedimentation vessel.

The resulting complex non-linear gradients having a short steep gradient section at the top, a long shallow section near the center, and a steep gradient at the bottom are difficult to make, and to make reproducibly and with precision. As such gradients are highly desirable for mixed particle separation, particularly subcellular and cellular fractionation, the need for the present invention exists.

In a biological sample, numerous different cell types may be present and each cell type has various subcellular organelles. In the field of functional and structural proteomics, one wishes to quantitatively detect changes in proteins. To enhance specificity, it is helpful to be measuring only one type of cell or portion of a cell to obtain a more accurate measurement.

There is also an urgent need to increase the number of proteins resolved using existing analytical methods such as two-dimensional electrophoresis, a similar need exists to assign to all proteins resolved a subcellular location, and a further need exists to develop quantitative cell fractionation to facilitate the detection and measurement of abundance changes in a larger number of cellular proteins in response to drugs, disease, and toxic agents. All of these several needs and requirements combine in a need for and uses for the development of methods and systems for making sets of precision density gradients of controlled composition. Prior to the present invention, no currently available methods and systems meet these requirements.

The present invention is exemplified by the fractionation of subcellular particles from mammalian cells and different types of mammalian cells. However, different cell types from other higher organisms are separable using the same basic techniques such as fractionating cells from plants, fungi, etc. In the field of subcellular fractionation, the techniques are applicable to all cells even including single celled organisms, yeast, bacteria, etc. As most infectious agents (known and unknown) are particles, the present invention is suitable for separation and isolation of such agents for research and diagnostic purposes. For example, viruses have different densities and different sedimentation coefficients. This permits easy separation and isolation of viruses by density gradient techniques.

While the present invention has been optimized for cellular and subcellular components from biological samples, the fractionation system of the present invention may also be used for many other materials for diverse purposes including the manufacture and separation of various particles for abrasives, catalysts, pigments, fluidized bed material and regeneration thereof (particularly for chemical manufacture), wastewater treatment, clays, vaccine, protein, DNA and other bioactive delivery systems, magnetic particles, food products, cosmetics etc.

In the majority of density gradient separations, the gradients and their chemical composition are designed to optimize the separation of one or a few particles types. This accounts for the very large number of different gradient recipes that have been published for subcellular fractionation. Those used for the isolation of mitochondria, for example, are usually quite different from those used to isolate nuclei. Traces of divalent cations are required to control nuclear swelling, whereas such ions may be deleterious to other subcellular particles. Low concentrations of nonionic detergents remove cytoplasmic contamination from nuclei, but are deleterious to the endoplasmic reticulum. Hence, no single procedure or gradient has been optimized for the systematic separation of the majority of subcellular particles.

Progress in molecular anatomy is now limited by the absence of methods for resolving subcellular components by high-resolution methods that are quantitative. High-resolution two-dimensional electrophoresis (2DE) is used to produce global maps of the proteins in extracts prepared by solubilizing whole cells or tissues. By careful control of the procedures employed, use of staining procedures which are quantitative, and computerized image analysis and data reduction, quantitative measurements of differences in the abundance of individual proteins of ±15% have been achieved (Anderson, N. Leigh, Nance, Sharron L., Tollaksen, Sandra L., Giere, Frederic A., and Anderson, Norman G., Quantitative Reproducibility of Measurements from Coomassie Blue-Stained Two-Dimensional Gels: Analysis of Mouse Liver Protein Patterns and a Comparison of BALB/c and C57 Strains. Electrophoresis 6: 592–599, (1985); Anderson, N. Leigh, Hofmann, Jean-Paul, Gemmell, Anne, and Taylor, John, Global Approaches to Quantitative Analysis of Gene-Expression Patterns Observed by Use of Two-Dimensional Gel Electrophoresis. Clin. Chem. 30: 2031–2036, (1984).

This technology allows changes in gene expression, as reflected in the abundance of individual proteins, to be studied under a wide range of conditions, and has led to the development of databases of protein abundance changes in response to a wide variety of drugs, toxic agents, and disease states. In such studies, large sets of data must be acquired and intercompared. Hence, all stages in one pharmaceutical study, for example, should be standardized for intercomparability. If cell fractionation is used in this work, then all of the fractionation techniques should be quantitatively intercomparable—a requirement necessitating gradients and separative procedures that are uniform, reproducible and identical.

An additional difficulty with 2DE mapping arises from the limited number of proteins detected. Maps of whole cells or tissues typically contain a thousand or more protein spots in sufficient abundance to allow each protein seen to be analyzed by mass spectrometry, identified and characterized. However, it is known that a much larger number of proteins are present in the tissue samples analyzed than is actually observed. The number of proteins present varies with cell or tissue type, and is believed to be up to ten or twenty times the number detected by present techniques. Different subcellular particles and the soluble fraction of the cell (the cytosol) contain many location-specific proteins which constitute only trace fractions of the total cell protein mass.

The total number of proteins resolved from one cell type or tissue could be very greatly increased if the 2DE analysis were done on cell fractions rather than on whole cell or tissue extracts, as has been previously demonstrated (Anderson et al., Electrophoresis 6:592–599, (1985)). Cell fractionation is generally done in density gradients. Hence, the development of improved density gradient methods will contribute to solving the problem of increasing the number of proteins resolved by 2DE.

If a drug effects study is to be done on cell fractions, the fractionation procedures must be quantitative, in the sense that the same organelles or even mixtures of organelles are present in the fractions to be intercompared. Further, the same gradient fraction should always represent the same fraction of those originally present. Thus, requirements for quantitation provide an additional incentive to the development of precision gradients.

The protein composition of tissues, such as liver, varies diurnally, hence all the tissues from one group of organisms are prepared at the same time of day, and, to be comparable, must be fractionated in parallel, on the same time schedule, and, if gradients are to be used, in identical gradients. Plants in particular respond to light and their metabolism as determined by protein abundance also differs with time of day. Further, gradient fraction recovery should be done from all gradients in parallel, under identical conditions. If the initial separations are done partly or entirely on a sedimentation rate basis, and if the recovered fractions are to then each to be isopycnicly banded, as is done in two-dimensional or s-$\rho$ fractionation, then these subsequence steps must also be carried out in parallel. There is therefore a need for systems for making a set of gradients simultaneously and repeatably.

Once a species of cellular or subcellular particle is isolated, there is a further need and interest in subfractionation. For example the inner and outer membranes of mitochondria have been isolated and studied. In many cases, this involves treatment of the isolated particles with a dissociating or reactive reagent, followed by centrifugation to remove the particles from that reagent. In the present invention, the process may be performed in one step by centrifuging particles through zones of disassociating reagents.

A flexible method for making gradient components from two solutions using mixing patterns is shown diagrammatically in FIG. 1. At each of the mixing levels 1–4 aliquots of each solution are mixed to produce intermediate solutions which, together with the parent solutions at that level, comprise a new level. If n is the number of solutions at one level, the next will include 2n–1 solutions. Any number of mixing levels can be used. An advantage of this method is that one can be certain that mixing a solution, such as 6 with an equal or unequal volume of solution 7, will produce solution 8 which will have a density between that of 6 and 7, and not outside the range of 6 to 7.

Thus, at each mixing level, with little effort compared to making a new solution, a mixture will be produced that will lie between, and if equal volumes are used, almost exactly between the two solutions mixed. This method is of great advantage when very shallow gradients are to be formed. If this process is continued through the five stages 1–5 shown, then a 17 step linear gradient will be formed at mixing level 5 from two starting solutions, providing equal volumes are mixed at each step involving two solutions.

Alternatively, by mixing unequal volumes of the two liquids, an intermediate of different proportions can be made which will always be intermediate between the two parent liquids. In this embodiment, there will be no need for additional intermediate levels formed by mixing a previous intermediate liquid with another liquid. All gradient components may be generated from various different volume mixtures of two parent liquids where each parent liquid represents opposite ends of the gradient being formed.

While mechanical gradient makers exist, it is very difficult to prepare gradients with fine differences precisely. Furthermore, such gradient makers usually do not make non-linear gradients in an acceptably controllable fashion.

Two variables may be introduced in the dilution pattern of FIG. 1 to make simple non-linear gradients. The first is to alter the ratios between components at one or more mixing steps to introduce either plateaus or sharp density increments (or decrements). The second is to vary the amount of each final component actually pipetted into the centrifuge tube.

The scheduled reagents may pipetted directly and rapidly into the centrifuge tubes, using either floats (WO 01/12507) or other means to prevent mixing between layers. One otherwise unused tube may contain for the sample, which is added after the gradient has diffused the scheduled amount to smooth the gradient. Integral to the system is a device for changing pipette tips at intervals not only to provide fresh uncontaminated tips, but also to change their capacity.

While the sedimentation vessel may be in many possible shapes and sizes, it is of particular interest to use sector tubes so that when centrifuged, the lines of sedimentation do not intersect with the centrifuge tube walls. One example of a sector tube is U.S. Pat. No. 2,878,994.

Figure 2:
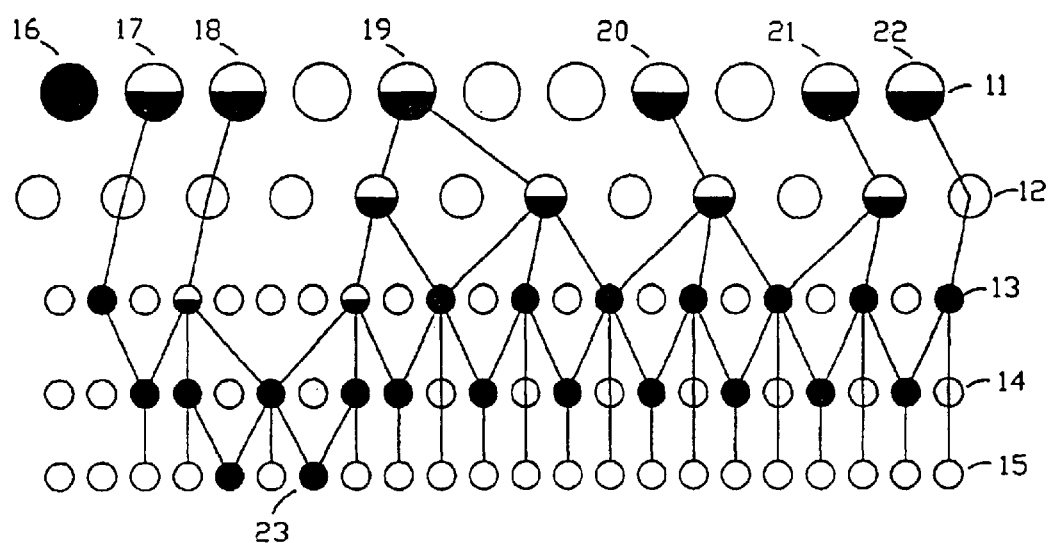
FIG. 2 shows a gradient component set and a mixing pattern for non-linear gradient construction.

As is illustrated diagrammatically in FIG. 2, very complex gradients can be produced by the selective use of dilution step combinations. These not only alter the gradient shape with regard to density, but also may have different reagents at different density zones. By increasing the number and diversity of the solutions in the starting series, very complex gradients may be formed. In FIG. 2 stages or rows 11–15 include seven starting solutions 16–22 which are of increasing density in number order, but may have very different compositions. Additionally, the density difference between them can be very different along the row. Equivolume mixtures are made according to the pattern indicated, and all blank circles represent positions not used. Used positions are either half black or completely black, and only vessels indicated as completely black are used as sources of liquid for pipetting into the centrifuge tubes. Thus the pipetting pattern can be complex and is best done under microprocessor control. Other types of gradients may be likewise formed. Non equivolume mixtures may be used to prepare the liquids used in preparing the gradients.

When pipetting to mix liquids for intermediate gradient components and to later form gradients, it is desirable to temperature control the entire system, preferably by refrigeration (~5° C.). In the presence of thermal gradients, rapid mixing and the irregular formation of physical and chemical gradients occurs. In addition, temperature affects the volume measurement of liquids being handled. This is particularly important for forming non-linear gradients and reagent containing zones in the gradient. It is even important in linear gradient formation as it effects the diffusion time needed. Even when using non-sedimenting reagents, as is preferred, the reagents will slowly diffuse at a rate that is affected by the temperature.

Figure 4:
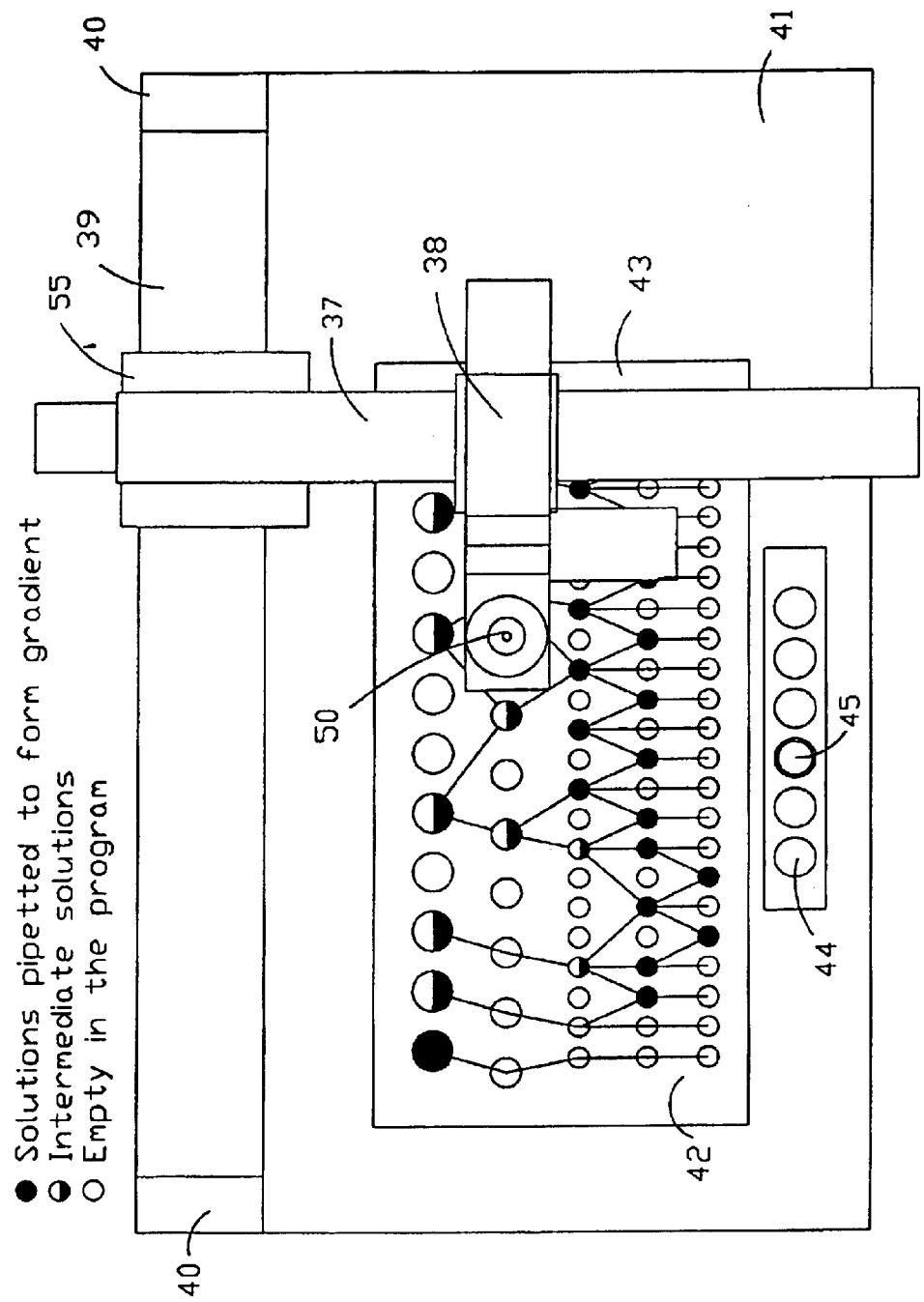
FIG. 4 is a top view of an automated gradient pipetter.

While the design shown in the FIGS. 1, 2 and 4 is adapted for equivolume measurements, they may be adapted to pipette unequal volumes to directly prepare the final gradient component liquids. In such a design, only two pipette tips are needed for preparation of the gradient components, and for each parent liquid. The system may employ two arms, each with its own pipette and computer control to prevent the arms from interfering with each other. Arms using radial moving motors are preferred to X and Y coordinate movement on rails if two automated pipetting devices are to be used. Optionally, different lines and pumps to move parent liquids to the tubes may be used. For actual preparation of the density gradient by layering gradient components, this may be done by a pipetting device with pipette tips changed or washed between adding of the gradient components.

A graph of the desired gradient or other information of how to form the gradient is entered into a computer which then directs the formation of intermediate liquids and their placement in a vessel to form the gradient.

One of the reasons for having different compositions throughout a gradient is that different particles have different requirements for stable separation and/or isolation. For example, in subcellular particle purification, ionic and osmotic requirements for each particle's optimal isolation differ from each other. Likewise, different portions of the density gradient may have essential cofactors, aggregating components, e.g. antibodies, receptors, optionally with detectable labels, that bind to a desired component, solvents and other disaggregating components, e.g. hydrolases, etc. Minor additions may be made to a gradient zone, for example, a few milligrams of an enzyme may be added dry to tube 23 in FIG. 2, without changing the gradient noticeably. Mixing of constituents may be done by rotational agitation of the plate, by mixing the liquid by movement, such as using a stir bar or impeller, or by repeated aspiration and dispensing pipetting mixtures up and down using the automatic pipetter.

Figure 7:
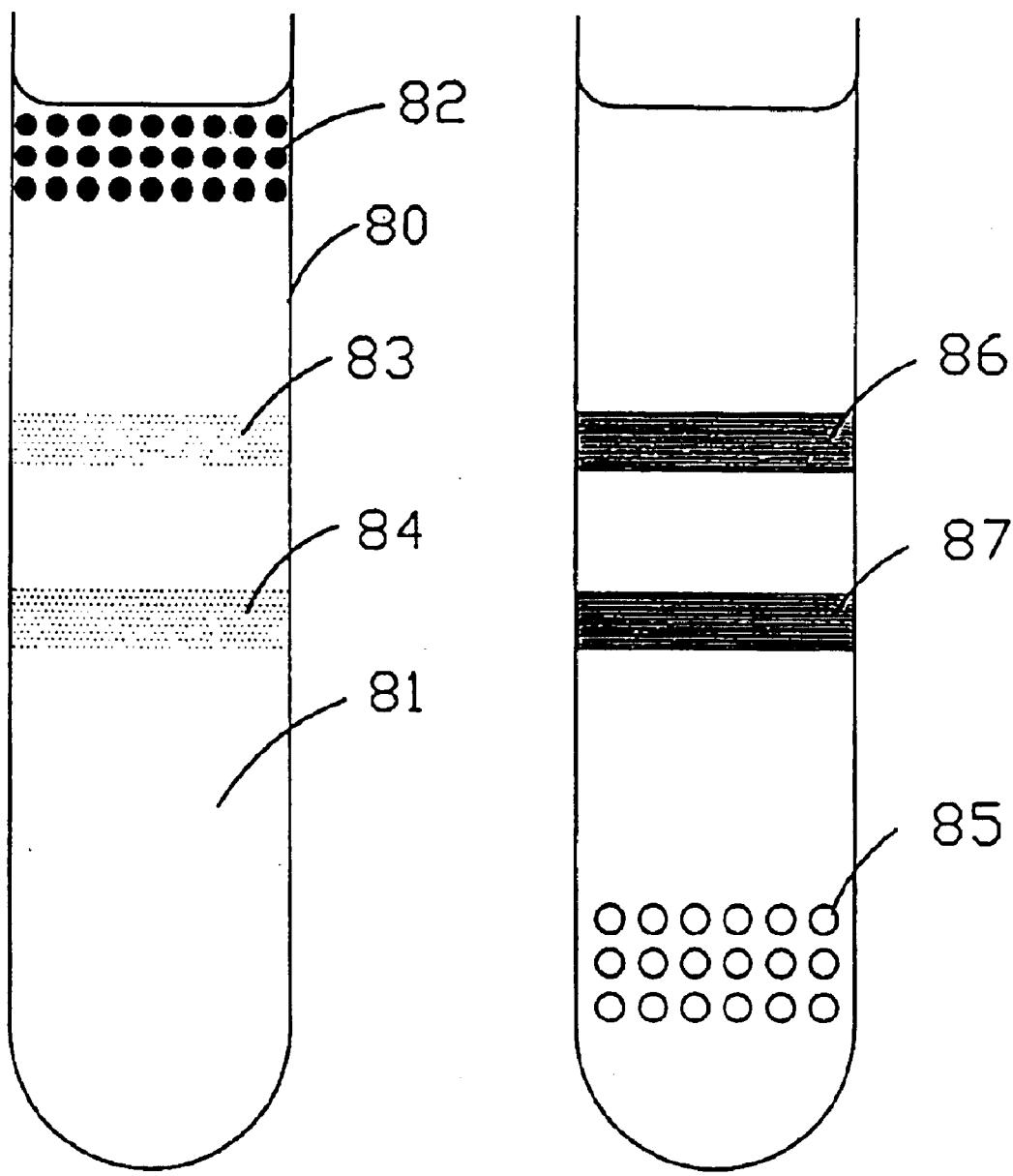
FIG. 7A shows diagrammatically non-sedimenting reagents in zones in a density gradient and particles in a sample zone about to be sedimented through said zones.
FIG. 7B shows diagrammatically the same gradient after sample particles have passed through the gradient, leaving reagent extractable substances in the reagent zones.

Distinct zones may be formed which remain almost stationary relative to sedimenting particles, providing the distinct zone constituents have sedimentation coefficients that are negligible relative to the sedimenting particles. For example, as shown diagrammatically in FIG. 7, a zone or region having a salt composition, osmotic pressure, or enzyme activity may be beneficial for the separation of certain subcellular components of a sample. FIG. 7A shows a centrifuge tube 80 containing a gradient 81 having reagent zones 83 and 84, composed of reagents having negligible sedimentation coefficients under the centrifugation conditions employed, and particle-containing sample zone 82. After centrifugation, as shown in FIG. 7B, the particles 85 have traversed the reagent zones, and have left behind extracted proteins in zones 86 and 87.

Gradients may also be prepared to contain increments of one component, which stabilizes the gradient, and a second, which sequentially extracts material from sedimenting particles. For example, gradients may be prepared using sucrose and sodium chloride which sequentially extract nuclei or other subcellular particles. A variety of different combinations may be prepared using the gradient producing and pipetting system described in which sedimenting particles undergo changes in pH, ionic composition, ionic composition or organic solvent concentration.

Density gradients may thus include not only gradients of dissolved solutes, but gradients of solvents including $D_2O$, dimethyl sulfoxide, or organic solvents including chlorinated and brominated alcohols.

To form reagent zones in the final gradient, one or more reagents are added to one or more solutions in the set of gradient components so that reagent zones are made in the final gradient. This forms a grid of gradient components. Ideally, the reagent will not change the density, volume or other undesired chemical properties of the gradient component. This is important to not affect the shape of the overall gradient. This can best be done by replacing a chemical in the gradient component with the reagent in proportions to not affect the other features of the final gradient.

Figure 3:
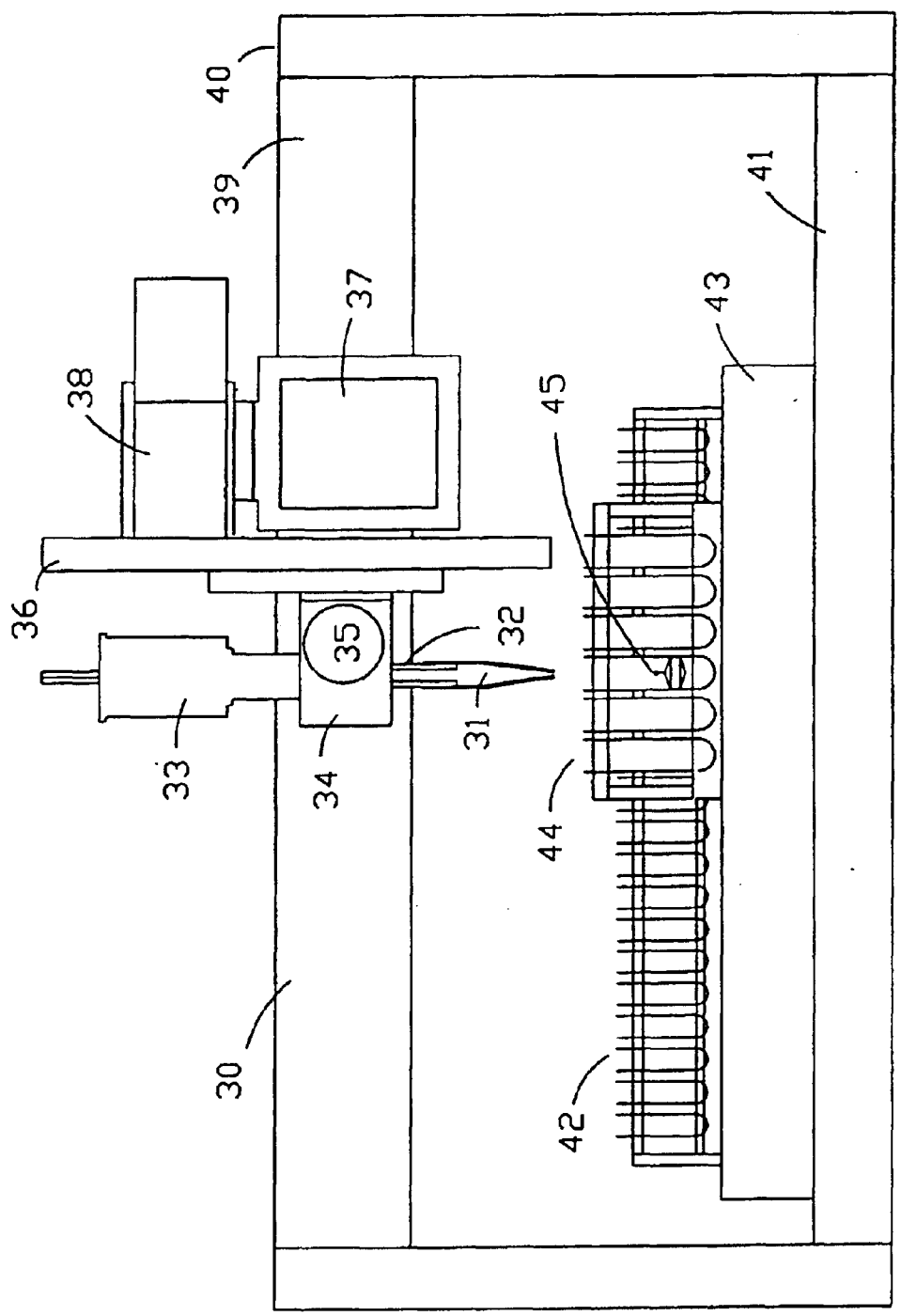
FIG. 3 is a side view of an automated gradient pipetter.

Reagents to be added in very small amounts, such as enzymes, detergents, solvents or salts may also be placed in otherwise unused positions on plate 42 of FIGS. 3 and 4, and added to gradient solutions as programmed. Unlike mechanical gradient makers, where the addition of a reagent would be at best difficult, the present invention is readily adapted to the addition of one or more reagents to one or more components of the gradient.

Detergents may be added as a single band to solubilize membrane bound particles or to prevent non-particle components from being membrane bound. By recovery of the band, proteins disassociated from particles may be isolated and purified. Particles without these bound components may be recovered from a different region of the gradient. The same will apply for solvents, salts, chaotropic or disaggregating agents (e.g. high concentrations of urea).

The pipetting machine is microprocessor-controlled, and measures and mixes all gradient components from an initial series of operator-made solutions. The intermediate mixtures may be further mixed by the pipetter by several cycles of solution withdrawal and expulsion controlled by the first phase of the pipetting program.

A pipette device can comprise a base on which the remaining parts are positioned, a plurality of movable or rotatable arms, supports and joints for supporting and positioning a plurality of pipettes and a receiver to hold the vessels in which the gradient is made. Movement of the arms can be along horizontal or vertical axes or planes. The movements can be controlled by a computer or microprocessor. The arms, supports and joints can be affixed directly to the base or may be attached to the base by an extendable member.

For automated formation of a gradient, a robot capable of moving a pipette or part of a pipette device accurately and with controllable working in three coordinates is used. With the robot under computer control, various simulation programs and other scheduling systems may be used to have the robot generate a large number of different gradients automatically.

For convenience, the pipette may have removable pipette tips that are readily replaceable within the system. The liquids used to form the gradient may be arrayed is separate vessels, such as tubes in a rack, or in different regions of an integral multiple container sheet, such as a multi-well plate. The robot is informed or senses the locations of all of the vessels or containers of gradient forming liquid and the location of the resulting vessel being filled by mixing or layering of two or more liquids. A number of simple computer programs can determine the patterns and schedules to be formed such as that shown in FIG. 2.

A separate container may be present or reserved for reagents for forming reagent-containing zone as gradient component(s), the final gradient and the sample to be added to and passed through the gradient. The layering of the gradient components to form the gradient may be done by a number of methods, including slow and careful layering one on top of another, but is preferably performed with the apparatus and techniques of WO 01/12507 which comprise floats 45 as shown in FIGS. 3 and 4 which decelerate fluids introduced above them and cause said fluids to flow slowly and evenly past the float, and to form sharp interfaces between successively introduced layers. As many different gradients will be used and numerous different gradient types are envisioned in the present invention, disposable vessels, sheets, pipette tips etc. are preferred. Plastic and glass materials are ideally suited for these purposes.

The pipetting machine is microprocessor-controlled, and measures and mixes all gradient components from an initial series of operator-made solutions. The intermediate mixtures are further mixed by the pipetter by several cycles of solution withdrawal and expulsion controlled by the first phase of the pipetting program.

In this arrangement the shape of the gradient is controlled by (a) the number, composition, and distribution pattern of the initial solutions used, (c) the mixing and source pattern employed, (d) the volumes of the aliquots used to make intermediate solutions, and (d) by the volumes actually pipetted out of each source vessel into the centrifuge tubes.

Much of the process may be automated. FIGS. 3 and 4 show diagrammatically a pipetting machine 30 in accordance with the present invention. The pipetting machine 30 includes a base 41 that supports a support plate 43 and vertical supports 40. The plate 42 is formed with apertures that support a plurality of tubes. The vertical supports 40 support a horizontal first track 39 that in turn supports a guide 55 that is adapted to selectively move back and forth along the first track 39 that in turn supports a guide 55 that is adapted to selectively move back and forth along the first track 39. Horizontal movement of the guide 55 along the first track 39 is effected by a motor (not shown).

A second track 37 extends from the guide 55 in a direction generally perpendicular to the first track 39. A vertical track 36 is supported on the second track 37 such that the vertical track 36 is selectively moveable along the horizontal length of the second track 37. Horizontal movement of the vertical track 36 along the second track 37 is effected by a stepping motor 38. A motorized syringe or pipette 33 is supported on the vertical track 36 for selective up and down movement along the vertical length of the vertical track 36. Up and down movement of the motorized pipette 33 is effected by a stepper motor 35.

The motorized pipette 33 includes a probe 32 able to pick up and release a disposable plastic tip 31. The motor controlling movement of the guide 55, the motor 38 and motor 35 are all controlled by a computer 95, shown in FIG. 5. The three dimensional movement allows the system to pipette solutions between tubes in plate 42, and other tubes arrayed behind them on the plate or rack 42, all containing gradient component solutions, and to transfer aliquots of the set of gradient producing solutions into the centrifuge tubes 44, into which the gradient components are loaded.

The motorized pipette 33 includes suction control (not shown) such that liquid from any of the tubes may be aspirated into and dispensed from the pipette back to any of the tubes.

In FIG. 4, a top view of the pipetting machine 30 is shown with pipette holder 50 positioned over one gradient solution tube. The solution tubes actually used are shown in black, with interconnecting lines indicating the source of mixture.

Figure 5:
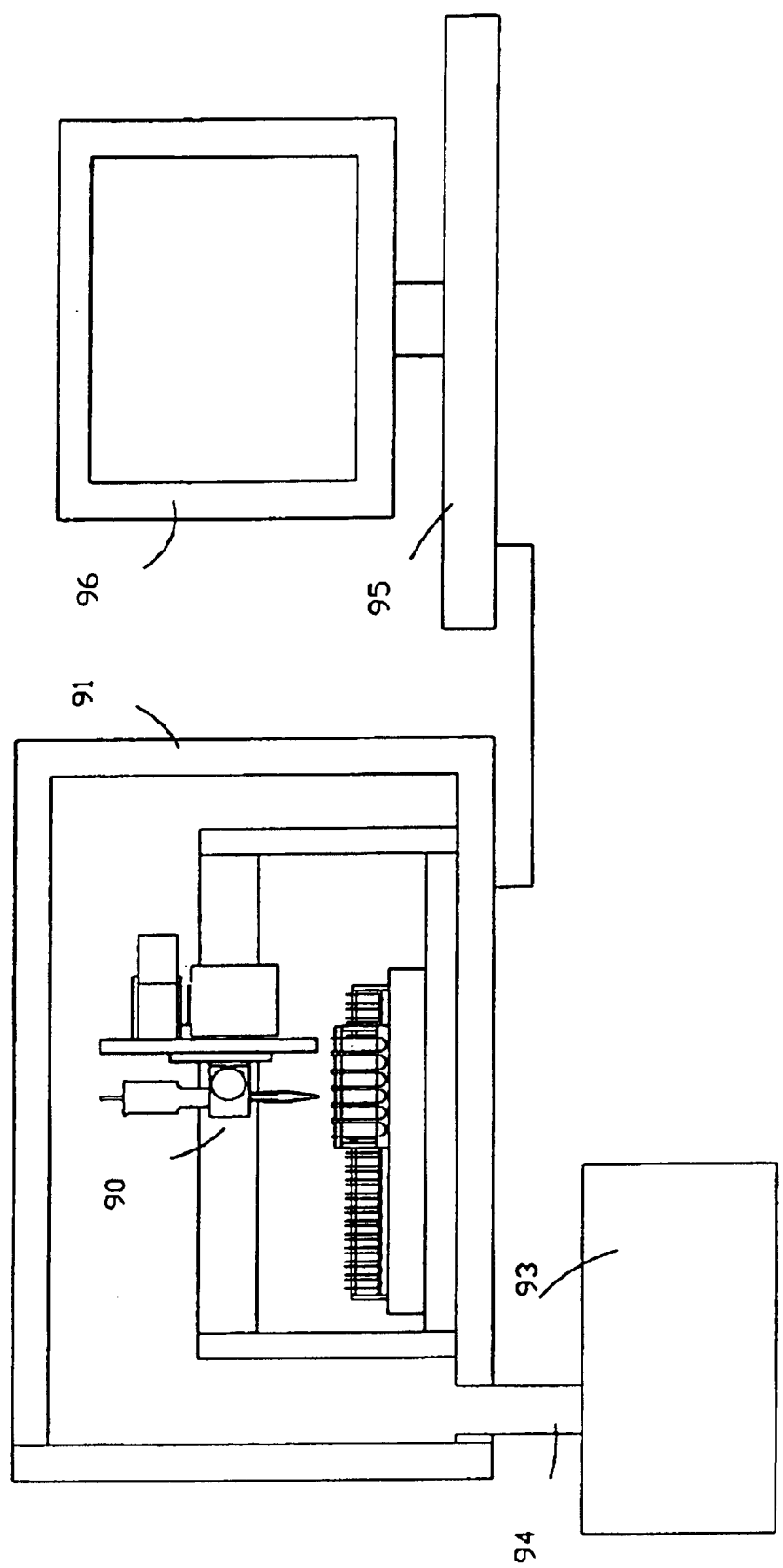
FIG. 5 shows diagrammatically an enclosed, refrigerated and microprocessor controlled pipetting system.

As shown in FIG. 5, the entire apparatus 90 is preferably enclosed in an insulated transparent temperature-controlled cabinet 91 to keep all reagents at a constant temperature, preferably at about 5 C using chilled air passed through connection 94 from chiller 93. Maintaining isothermal conditions are important to avoid thermal currents mixing the gradient. Operation of the apparatus is controlled by computer 95 and control programs are observed on CRT 96.

The computer 95 may be a specialized computer programmed to control the pipetting machine 30 or may be a general-purpose computer such as a standard personal computer with software adapted to control the pipetting machine 30. The computer 95 includes an input device (not shown), such as a keyboard and/or mouse that enables a user to enter information that enables the pipetting machine 30 to produce any desired density gradient within the tubes 44. A user inputs information specifying the density required in each layer of a density gradient, such as the density gradient shown graphically in FIG. 8, and described in greater detail below.

Figure 9:
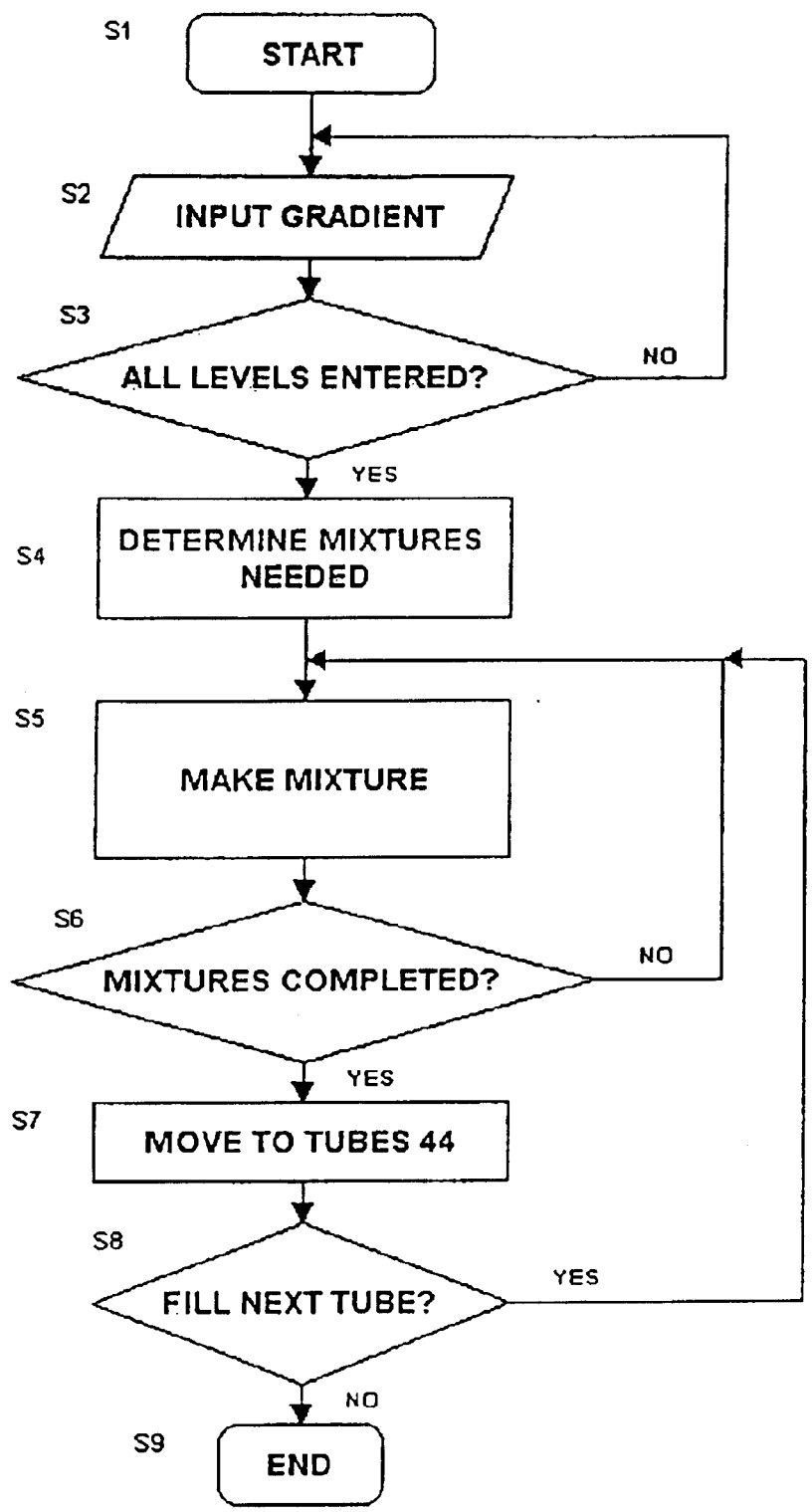
FIG. 9 is a flow chart of the operation of the apparatus in the present invention.
Figure 10:
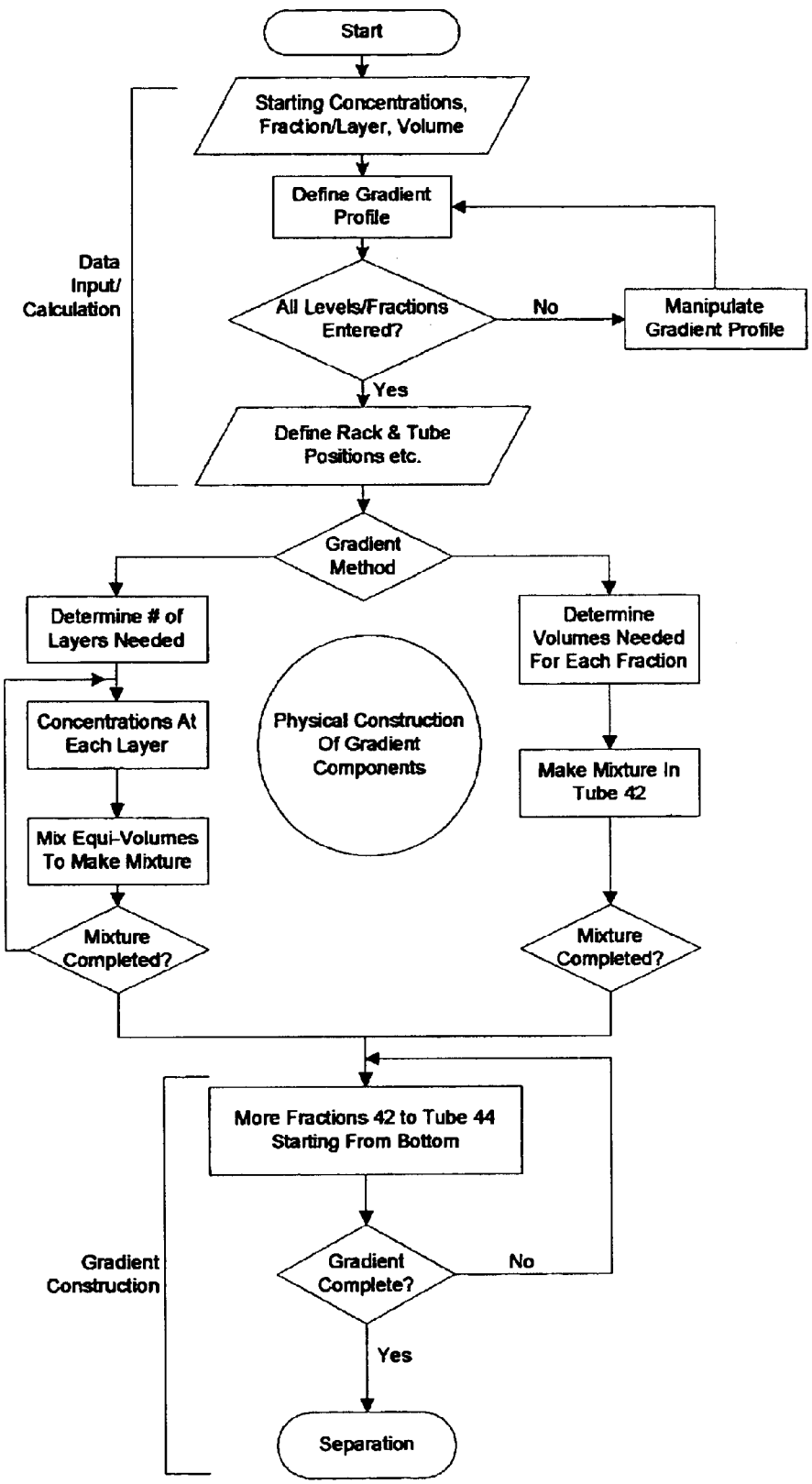
FIG. 10 provides another flow chart of activities in preparing a gradient.

The software installed in the computer 95 is configured to control the pipetting machine 30 in a flexible manner. FIG. 9 is a flowchart showing one example of operational steps conducted by the computer 95 to control the pipetting machine 30. At step S1, the computer 95 initializes with a start-up procedure. After start-up, a user is prompted at step S2 to enter parameters regarding one layer of the desired density gradient. In Step S3, the computer 95 determines whether all data with respect to the desired gradient layers have been inputted. If more information regarding a layer needs to be inputted, then step S2 is repeated. If all information regarding the layers of the density gradient have been inputted, then operation proceeds to step S4 where the computer 95 is directed to calculate all necessary intermediate solutions necessary to produce the final density gradient.

At step S5, the computer 95 manipulates the pipetting machine 30 to deliver appropriate liquids to one of the intermediate tubes to create an intermediate solution. At step S6, a decision is made determining whether or not all intermediate solutions or mixtures have been produces. If more mixtures need to be produced, step S5 is repeated. If all intermediate solutions have been produced, then step S7 is performed. At step S7, each intermediate solutions is loaded one by one, into the appropriate tube 44 to produce the density gradient.

At step S8, a decision is made determining whether of not another identical density gradient is to be produced. If so, steps S5, S6 and S7 are repeated as necessary. Once all required tubes 44 are supplied with the requested density gradients, operation moves to step S9 where the computer 95 stops and the program ends or returns to a standby state.

It should be understood that the operation described above is only one example of the control of the operation of the pipetting machine 30. Other algorithms and operational steps are possible. For instance, the computer may have a graphical interface wherein the density gradient may be inputted by manipulation of a curve on a graph similar to that shown in FIG. 8. The computer may be pre-programmed with an index having information relating to many possible variations of intermediate solutions to be formed in the production of various density gradients. As well, the computer 95 may alternatively be pre-programmed with a plurality of density gradient profiles similar to the information displayed in FIG. 8 such that a user chooses one of the plurality of density gradient profiles for automatic production of one or more density gradients delivered to the tubes 44.

While the present invention has been optimized for cellular and subcellular components from biological samples, the fractionation system of the present invention may also be used for many other materials for diverse purposes including the manufacture and separation of various particles for abrasives, catalysts, pigments, fluidized bed material and regeneration thereof particularly for chemical manufacture), wastewater treatment, clays, vaccines, proteins, DNAs and other bioactive delivery systems, magnetic particles, food products, cosmetics etc.

The various components of an invention of interest can be ordered at the benchtop using a rack that holds multiple containers. The rack can be any horizontally oriented structure having a plurality of means for positioning individual gradient components in an upright position. The means for restraining and positioning the components could be spaces to receive vessels in the structure or receptacles therein. The gradient components can be arranged in particular configurations, for example based on the expected location thereof in the gradient. Thus, a component forming an intermediate layer may be positioned in the rack between components that will comprise a layer above and a layer below the intermediate layer. Other configurations can be contemplated and arranged to facilitate access to the components and gradient formation.

EXAMPLE 1

Gradient Set-Up

A method and system for preparing solutions for a making a 17 step gradient is illustrated diagrammatically in FIG. 1. The tubes may be either separate vessels as shown, or may be molded into one or more multiwelled plate(s). Rows 1–5 of tubes or containers are arranged so that the first row contains two tubes, the second 3, the third 5, the fourth 9, and the fifth 17, i.e., each row contains one less than double number in the preceding row. The present invention may continue the process with as many rows as desired for all or part of each row to make as fine of a gradient and in whatever proportions desired. From each row liquid is pipetted from adjacent tubes to the one between in the succeeding rows to produce a mixture, and is pipetted into the one directly below without addition except as described below. If the light end of the gradient is in tube 6, and the dense end is in tube 7, the result is row 5 in which tube 9 is unmodified liquid from tube 6, and tube 10 is unmodified liquid 7, with all intermediate tubes containing a linearly incremental gradient between the two, providing all succeeding rows have been mixed in volumetrically equal proportions.

With 15% w/w sucrose in tube 6 of FIG. 1 and 48% sucrose w/w in tube 7, linear gradients suitable for fractionating rat liver homogenates may be prepared. Using 4 ml samples of a 10% homogenate of rat liver prepared in 0.25 M sucrose, and layered over the gradient using the floats described in U.S. patent application Ser. No. 09/551,314 filed Apr. 18, 2000, the homogenate may be fractionated into soluble phase, endoplasmic reticulum, and mitochondria by centrifuging for twenty minutes at 4° C., at a rotor speed of 20,000 rpm.

EXAMPLE 2

Non-Linear Gradient Formation

Figure 8:
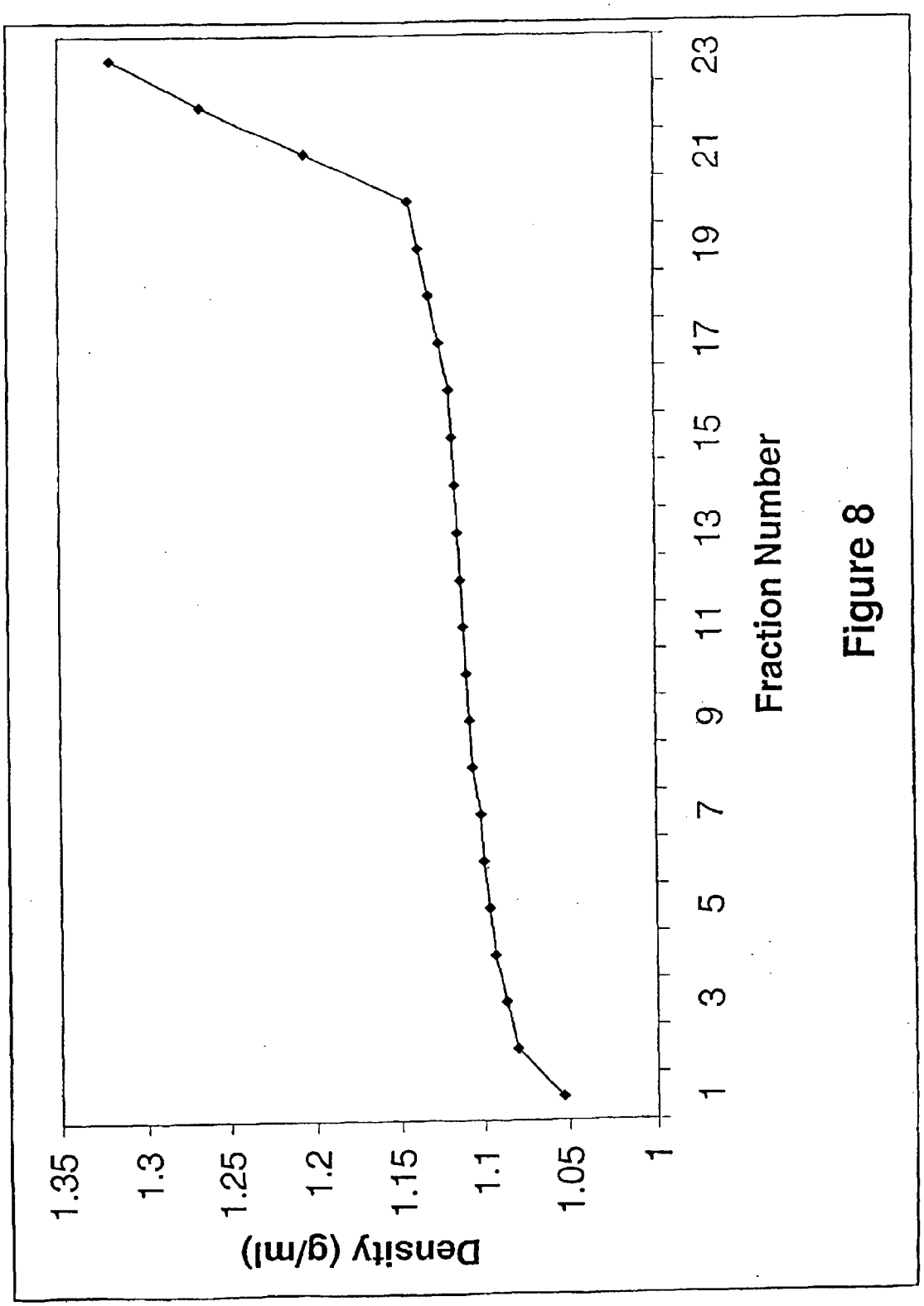
FIG. 8 is a plot of density vs. fraction number for a non-linear gradient.

A non-linear complex gradient, shown in FIG. 8, was prepared using the method and system illustrated in FIG. 2. This gradient resolves the cytosol, endoplasmic reticulum, mitochondria and nuclei, using an iodinated gradient material such as Iodixanol®. This system uses 5 rows 11–15 of vessels or tubes having decreasing volumes in descending rows. The initial Iodixanol® concentrations are for tube 16, 10%; 17, 15%; 18, 17.5%; 19, 20%; 20, 22.5%; 21, 27%; and 22, 50% w/v. The pipetting scheme is indicated by the cross connections between the circles. Only a fraction of the tubes is required to produce a given complex gradient. This plate yields 22 gradient steps. In the instance shown, only two tubes are required in row 15. The 22-step gradient is pipetted out of the vessels shown in solid black using the microprocessor-controlled pipetter.

FIG. 8 shows the non-linear gradient produced using the plate and diagram of FIG. 2 giving physical density (g/mL) as a function of step numbers. The raw data is given in the following Table 1.

TABLE 1

IODIXANOL ® GRADIENT

| Gradient Fraction Number | Starting Concentration (% Iodixanol ®) | Concentration of Iodixanol ® in Gradient | Densities (g/ml) |
| --- | --- | --- | --- |
| 1 | 10 | 10 | 1.0533 |
| 2 | 15 | 15 | 1.0799 |
| 3 |  | 16.25 | 1.0866 |
| 4 | 17.5 | 17.5 | 1.0932 |
| 5 |  | 18.125 | 1.0966 |
| 6 |  | 18.75 | 1.0999 |
| 7 |  | 19.09 | 1.1015 |
| 8 | 20 | 20 | 1.1066 |
| 9 |  | 20.3125 | 1.1082 |
| 10 |  | 20.625 | 1.1099 |
| 11 |  | 20.9375 | 1.1115 |
| 12 |  | 21.25 | 1.1132 |
| 13 |  | 21.5625 | 1.1149 |
| 14 |  | 21.875 | 1.1165 |
| 15 |  | 22.1875 | 1.1182 |
| 16 | 22.5 | 22.5 | 1.1199 |
| 17 |  | 23.625 | 1.1259 |
| 18 |  | 24.75 | 1.1319 |
| 19 |  | 25.875 | 1.1379 |
| 20 | 27 | 38.5 | 1.2052 |
| 22 | 50 | 50 | 1.2665 |
| Cushion | 60 | 60 | 1.3198 |

Density of 0.25 M sucrose = 1.032 (Sample layer)
Iodixanol Density = (concentration × 0.00533) + 1

Numerous gradient materials may be employed in addition to those described. It will be understood that various modifications may be made to the embodiments disclosed herein. Therefore, the above description should not be construed as limiting, but merely as examples of preferred embodiments. Those skilled in the art will envision other modifications within the scope and spirit of the claims appended hereto.

EXAMPLE 3

Gradient Formation with Controlled Volumes

A non-linear complex gradient, shown in FIG. 8, was prepared using an alternative method and system from that in Example 2. This system uses two parent solutions of 10% and 60% Iodixanol®. Twenty-three tubes are used each to represent the exact 22 gradient components and one tube for the 60% cushion. The proportions of each parent solution needed to prepare each solution are calculated by a computer that controls a two-arm pipetting device (one pipette for each parent solution). Once the 22 solutions are prepared, the 22-step gradient is pipetted out of the vessels using the microprocessor-controlled pipetter with a clean pipette tip changed for each. An indistinguishable gradient producing comparable results to that of Example 3 results.

All patents and references cited herein are explicitly incorporated by reference in their entirety.

REFERENCES

Price, C. A. Centrifugation in Density Gradients. Academic Press, N.Y. 1982 430 pp.

Scheeler, P. Centrifugation in Biology and Medical Science. John Wiley & Sons N.Y. 1981 269 pp.

Anderson, N. G. A simple method for observing refractive index gradients in liquids. Biochim. Biophys. Acta 25:418,1957.

Albright, J. F., and Anderson, N. G. A method for the rapid fractionation of particulate systems by gradient differential centrifugation. Exptl. Cell Research 15: 271–81, 1958.

Anderson, N. G., Bond, H. E., and Canning, R. E. Analytical techniques for cell fractions. I. Simplified gradient elution programming. Analyt. Biochem. 3: 472–478, 1962.

Anderson, N. G., and Rutenberg, E. Analytical techniques for cell fractions. A simple gradient-forming apparatus. Anal. Biochem. 21: 259–265, 1967.

Luthe, D. S. A simple technique for the preparation and storage of sucrose gradients. In: Anal Biochem 135:230–2, 1983.

Clark, A. G. Gellen J W Hydrostatically balanced gradient-formers: programming of gradients. Anal Biochem 103:94–100, 1980.

Sartory, W. K., Halsall H B Design of a generalized n-solute mixing-chamber gradient generator. In: Anal Biochem 88:539–51,1978.

McRee, D. Inexpensive apparatus for preparation of multiple discontinuous gradient. In: Anal Biochem 87:638–52, 1978.

Sheeler, P, Doolittle M H, White H R Method and apparatus for producing and collecting a multiplicity of density gradients. Anal Biochem 87:612–21, 1978.

Michov, B. M. A concentration gradient system. Anal Biochem 86:432–42, 1978.

Corless, J. M. Simple and inexpensive fabrication of small-volume density gradients. Anal Biochem 84:251–5, 1978.

Shearer, G., Jr. A syringe-based gradient former for linear and exponential gradients. In: Anal Biochem., 221:397–400, 1994.

Graham, J., Ford, T, Rickwood D The preparation of subcellular organelles from mouse liver in self-generated gradients of iodixanol. Anal Biochem 220:367–73, 1994.

Ford, T. Graham, J., Rickwood, D. Iodixanol: a nonionic iso-osmotic centrifugation medium for the formation of self-generated gradients.: Anal Biochem 220:360–6, 1994.

Davis P. B., Pearson C. K. Characterization of density gradients prepared by freezing and thawing a sucrose solution. Anal Biochem 91:343–9, 1978.

Liedtke, R., Mosebach, K. O. An apparatus for density gradient forming and nonpuncturing fractionation. Anal Biochem 62:377–85, 1974.

Lange C. S., Liberman, D. F. A semiautomated system for the production and analysis of sucrose density gradients. Anal Biochem 59:129–45, 1974.

Hopkins, T. R. Another density gradient fractionator. Anal Biochem 53:339–41, 1973, Siakotos, A. N., Pennington, K., McInnes, A. New loading system for preparing density gradients for swinging-bucket rotors using programmed gradient pumps. In: Anal Biochem 43:32–41, 1971.

Wallach, D. F., A simple system for rapid generation of duplicate density gradients, Anal Biochem 37:138–41, 1970.

Shore S. L., Phillips D. J., Reimer C. B. Preformed frozen sucrose gradients—a new laboratory aid. Anal Biochem 31:114–7, 1969.

Margolis, J. A versatile gradient-generating device. Anal Biochem., 27:319–22, 1969.

Leif, R. C. Density gradient system. II. A 50 channel programmable undulating diaphragm peristaltic pump. Anal Biochem 25:283–96, 1968.

Leif, R. C. Density gradient system. I. Formation and fractionation of density gradients. Anal Biochem 25:271–82, 68.

Ayad, S. R., Bonsall, R. W., Hunt, S. A simple method for the production of accurate linear gradients using a constant-speed peristaltic pump. Anal. Biochem. 2:533–5, 1968.

Birnie, G. D., Harvey, D. R. A simple density-gradient engine for loading large-capacity zonal ultracentrifuge rotors. Anal. Biochem. 22:171–4, 1968.

Anderson, N. G., Rutenberg, E. Analytical techniques for cell fractions. VII. A simple gradient-forming apparatus. Anal. Biochem. 21:259–65, 1967.

Samis, H. V. Jr. A simple density gradient generator. Anal Biochem 15:355–7, 1966.

Morand, J. N., Kent, C. A one-step technique for the subcellular fractionation of total cell homogenates. Anal. Biochem. 159:157–62, 1986.

Coombs, D. H., Watts, N. R. Generating sucrose gradients in three minutes by tilted tube rotation.: Anal. Biochem. 148:254–9, 1985.

Samuels, S., A continuous density gradient apparatus for use in zonal ultracentrifuges. Anal. Biochem. 41:164–7, 1964.

Anderson, N. Leigh, Nance, Sharron L., Tollaksen, Sandra L., Giere, Frederic A., and Anderson, Norman G., Quantitative reproducibility of measurements from Coomassie Blue-stained two-dimensional gels: Analysis of mouse liver protein patterns and a comparison of BALB/c and C57 strains. Electrophoresis 6: 592–599, 1985.

Anderson, N. Leigh, Hofmann, Jean-Paul, Gemmell, Anne, and Taylor, John, Global approaches to quantitative analysis of gene-expression patterns observed by use of two-dimensional gel electrophoresis. Clin. Chem. 30: 2031–2036, 1984.

Anderson, N. L., Giere, F. A., Nance, S. L., Gemmell, M. A., Tollaksen, S. L., and Anderson, N. G. Effects of toxic agents at the protein level: Quantitative measurement of 213 mouse liver proteins following xenobiotic treatment. Fund. Appl. Tox. 8: 38–50, 1987.

What is claimed is:

1. A method for forming a complex non-linear liquid gradient, containing a second type of gradient of a different constituent, comprising;
preparing an intermediate-level gradient component by mixing a lower-level gradient component with a higher-level gradient component,
preparing a secondary intermediate-level gradient component by mixing the intermediate-level component with another gradient component,
preparing components for the second type of gradient, and
layering said intermediate-level gradient component, said secondary intermediate-level gradient component and the components of said second type of gradient to form said complex non-linear liquid gradient containing said second type of gradient within it.

2. The method of claim 1 wherein said intermediate-level gradient component and said secondary intermediate-level gradient component are layered in contact with each other.

3. The method of claim 1 wherein at least one gradient component contains a non-sedimenting reagent capable of reacting with a sample passing through that gradient component.

4. The method of claim 1 wherein at least one gradient component contains a readily detectable constituent capable of determining the location of said gradient component in the liquid gradient.

5. A method for fractionating a particulate material containing a plurality of particles comprising;
supplying a particulate material to the vessel containing a complex non-linear liquid gradient produced by the method of claim 1,
sedimenting the particulate material through the liquid gradient to separate particles into groups, and
recovering at least one group of particles.

6. The method of claim 5 wherein the particulate material is a sample.

7. The method of claim 6 wherein the group of particles recovered are individual cells or subcellular particles.

8. The method of claim 5 further comprising separately recovering at least two different groups of particles.

9. The method of claim 1 wherein at least four gradient components are present, at least two of which are intermediate-level gradient components or secondary intermediate-level gradient components and no more than two are not intermediate-level gradient components.

10. The method of claim 9 wherein at least six gradient components are present, at least four of which are intermediate-level gradient components or secondary intermediate-level gradient components and no more than two are not intermediate-level gradient components.

11. A method for forming a complex non-linear liquid gradient from a plurality of gradient components comprising;
preparing an intermediate level gradient component by mixing a lower level gradient component with a higher level gradient component,
preparing a secondary intermediate level gradient component by mixing the intermediate level component with a different gradient component, and
layering plural gradient components to form said complex non-linear liquid gradient,
wherein at least two components used in said liquid gradient differ by less than about 1.25%,
wherein said intermediate level gradient component and said secondary intermediate level gradient component differ by are two of said plurality of gradient components used in said liquid gradient.

12. The method of claim 11 wherein said at least two liquid gradient components differ by less than about 0.625%.

13. The method of claim 11 wherein at least one of the gradient components contains a non-sedimenting reagent capable of reacting with a sample passing through that gradient component.

14. The method of claim 11 wherein at least one of the gradient components contains a readily detectable component capable of determining the location of said gradient component in the liquid gradient.

15. A method for fractionating a particulate material containing a plurality of particles comprising;
supplying a particulate material to the vessel containing a complex non-linear liquid gradient produced by the method of claim 11,
sedimenting the particulate material through the liquid gradient to separate particles into groups, and
recovering at least one group of particles.

16. The method of claim 15 wherein the particulate material is a biological sample.

17. The method of claim 16 wherein the group of particles recovered are individual cells or subcellular particles.

18. The method of claim 15 further comprising separately recovering at least two different groups of particles.

19. The method of claim 11 wherein at least four gradient components are present, at least two of which are intermediate level gradient components or secondary intermediate level gradient components and no more than two are not intermediate level gradient components.

20. The method of claim 19 wherein at least six gradient components are present, at least four of which are intermediate level gradient components or secondary intermediate level gradient components and no more than two are not intermediate level gradient components.

21. A method for forming a complex non-linear liquid density gradient from a plurality of gradient components comprising;
    preparing an intermediate level gradient components by mixing a lower level gradient component with a higher level gradient component,
    preparing a secondary intermediate level gradient component by mixing the intermediate level component with a different gradient component, and
    layering plural gradient components to form said complex non-linear liquid density gradient,
    wherein at least two components used in said liquid gradient differ in density by less than about 0.0017 g/ml.
    wherein said intermediate level gradient component and said secondary intermediate level gradient component differ by are two of said plurality of gradient components used in said liquid gradient.

22. The method of claim 21 wherein said at least two liquid gradient components differ by less than about 0.0034 g/ml.

23. The method of claim 21 wherein at least one of the gradient components contains a non-sedimenting reagent capable of reacting with a sample passing through that gradient component.

24. The method of claim 21 wherein at least one of the gradient components contains a readily detectable component capable of determining the location of gradient component in the liquid gradient.

25. A method for fractionating a particulate material containing a plurality of particles comprising;
    supplying a particulate material to the vessel containing a complex non-linear liquid gradient produced by the method of claim 21,
    sedimenting the particulate material through the liquid gradient to separate particles into groups, and
    recovering at least one group of particles.

26. The method of claim 25 wherein the particulate material is a biological sample.

27. The method of claim 26 wherein the group of particles recovered are individual cells or subcellular particles.

28. The method of claim 25 further comprising separately recovering at least two different groups of particles.

29. The method of claim 21 wherein at least four gradient components are present, at least two of which are intermediate level gradient components or secondary intermediate level gradient components and no more than two are not intermediate level gradient components.

30. The method of claim 29 wherein at least six gradient components are present, at least four of which are intermediate level gradient components or secondary intermediate level gradient components and no more than two are not intermediate level gradient components.

* * * * *